United States Patent
Carr et al.

(10) Patent No.: US 6,207,108 B1
(45) Date of Patent: *Mar. 27, 2001

(54) PEROXYGEN COMPOSITIONS

(75) Inventors: Graham Carr; Alun Pryce James, both of Liverpool (GB)

(73) Assignee: Solvay Interox Limites (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,535
(22) PCT Filed: Jun. 15, 1995
(86) PCT No.: PCT/GB95/01398
  § 371 Date: Feb. 28, 1997
  § 102(e) Date: Feb. 28, 1997
(87) PCT Pub. No.: WO95/34537
  PCT Pub. Date: Dec. 21, 1995

(30) Foreign Application Priority Data

Jun. 16, 1994 (GB) .................................................. 9412051

(51) Int. Cl.$^7$ ...................................................... A61L 2/00
(52) U.S. Cl. ...................... 422/28; 252/186.38; 424/616; 510/367; 510/375; 514/547; 562/2
(58) Field of Search ............................ 514/547; 424/616; 422/28; 252/186.38; 562/2; 510/367, 375

(56) References Cited

U.S. PATENT DOCUMENTS

| | | | |
|---|---|---|---|
| 4,681,592 | * | 7/1987 | Hardy et al. ............................. 8/111 |
| 5,139,788 | * | 8/1992 | Schmidt ................................. 424/616 |
| 5,200,189 | * | 4/1993 | Oakes et al. .......................... 424/405 |
| 5,368,867 | * | 11/1994 | Da Silva et al. ...................... 424/616 |

FOREIGN PATENT DOCUMENTS 0 166 571    1/1986   (EP) .
0 426 217 A2 5/1991   (EP) .

OTHER PUBLICATIONS

Lion et al., Bull. Soc. Chim. Belg. 1991, vol. 100, pp. 555–559.
Nedelec et al., Synthesis, 1976, pp. 821–823.

* cited by examiner

*Primary Examiner*—Krisanne Thornton
(74) *Attorney, Agent, or Firm*—Larson & Taylor, PLC

(57) ABSTRACT

Storage stable, aqueous acidic solutions having a pH in the range of from 1 to 5 comprising at least one ester peracid having general formula $$R\text{---}O\text{---}\overset{O}{\underset{\|}{C}}\text{---}(CH_2)_{\overline{x}}\text{---}CO_3H,$$

where R represents an alkyl group having from 1 to 4 carbons and x equals 1 to 4, are provided. The solutions can be prepared by contacting an aqueous solution of a carboxylic compound having general formula $$R\text{---}O\text{---}\overset{O}{\underset{\|}{C}}\text{---}(CH_2)_{\overline{x}}\text{---}\overset{O}{\underset{\|}{C}}\text{---}OH,$$

where x is from 1 to 4 and R represents an alkyl group having from 1 to 4 carbons with an inorganic peroxygen compound, preferably hydrogen peroxide, at a pH of less than 4 until at least some ester peracid is produced, and thereafter adjusting the pH to be in the range of from 1 to 5, if necessary.

26 Claims, No Drawings

PEROXYGEN COMPOSITIONS

This invention concerns peroxygen compositions. More specifically, this invention concerns solutions of peracids, and still more specifically, this invention concerns solutions of ester peracids.

It is well known that certain classes of compound exert a very strong microbicidal effect which renders them suitable for use as disinfectants in a wide range of applications, especially domestic and industrial hard surface disinfection. One of the most commonly employed compounds is sodium hypochlorite solution, because it is readily available at low cost and is reasonably effective as a disinfectant over short contact times. In recent years, however, there has been increasing concern expressed at the possible environmental consequences of the use of hypochlorite solutions, including the possible formation of chlorinated organic compounds, such as trihalomethanes, and so attempts have been made to identify alternative disinfectants.

One group of chemicals which it has hitherto been proposed to employ as an alternative to hypochlorite disinfectants comprises organic peroxygen compounds, particularly aliphatic $C_1$ to $C_3$ peracids such as peracetic acid. Although very effective microbicides, some people find the odour of these aliphatic peracids to be offensive or irritating, and so for applications in which the disinfectant is likely to be employed in the proximity of people, it is desirable to find alternative disinfectants.

Many disinfectant compositions, particularly household disinfectants employ a concentrated solution of disinfectant which is diluted to the required concentration in use. Many such concentrated solutions employ water as the solvent on account of its low cost, ready availability and ease of safe handling compared with organic solvents. It is obviously desirable that the disinfectant forms a single phase system in the concentrated solution because this avoids the need for the solution to be agitated before use. The formation of a single phase system reduces the possibility of the disinfectant becoming unevenly distributed throughout the composition and hence the possibility of inadequate or excessive dosing of the disinfectant.

Ester peracids are known in the prior art. For example, European Patent application No. EP-A-0 166 571 teaches the use of ester peracids of the general formula $[RX]_m AOOH$, where R is hydrocarbyl or alkoxylated hydrocarbyl, X is a heteroatom moiety, preferably oxygen, A is a wide range of organic moieties containing one or two carbonyl groups and m is one or two, for use in bleaching and laundry applications.

European Patent application No. EP-A-0 426 217 teaches the use of ester peracids of the general formula $X-O_2C-A-CO_3H$, where A is a C1 to C12 alkyl, aryl or alkaryl radical and X is a C1 to C20 alkyl, aryl, alkyl aryl radical, optionally including a heteroatom, for use in bleaching and cleaning systems.

Both French Patent application no. 2324626 and a paper by Nedelec et al, Synthesis, 1976, pp821–3 teach a method for the preparation and isolation of ester peracids from the reaction between acid chlorides and hydrogen peroxide in organic solvents.

A paper by C. Lion et al, Bull. Soc. Chim. Belg. 1991, 100, pp555–559 discloses the preparation and isolation of ester peracids by the reaction between ester acid and hydrogen peroxide in the presence of high concentrations of sulphuric acid, and quenching into ice. The ester peracids so produced are employed in the destruction of toxic organophosphorus compounds in aqueous alkaline solution.

None of the prior art references specifically disclose the storage stable, aqueous acidic ester peracid solutions of the present invention, or the use of solutions of such ester peracids as disinfectants.

It is an objective of the present invention to provide novel storage stable, aqueous acidic ester peracid solutions.

It is another objective of the present invention to provide a peracid microbicide with reduced odour compared with C1 to C3 aliphatic peracids.

It is yet another objective of the present invention to provide a method for preparing storage stable, aqueous acidic ester peracid solutions.

It is a further objective of the present invention to provide a method for disinfecting using low odour peracids.

According to the present invention, there are provided storage stable, aqueous acidic solutions having a pH in the range of from 1 to 5 comprising at least one ester peracid having the general formula:

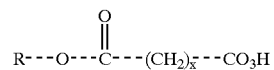

where R represents an alkyl group having from 1 to 4 carbons and x is from 1 to 4.

According to another aspect of the invention, there is provided a process for preparing storage stable, aqueous acidic solutions comprising at least one ester peracid, characterised in that the process comprises contacting an aqueous solution of one or more carboxylic compounds having the general formula:

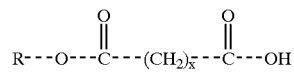

where x is from 1 to 4, R represents an alkyl group having from 1 to 4 carbons and x is from 1 to 4 with an inorganic peroxygen compound at a pH of less than 4, preferably 3 or less, until at least some ester peracid has been produced and, thereafter, where the pH of the resultant ester peracid solution produced is less than 1, its pH is adjusted to be in the range of from 1 to 5.

A further aspect of the invention provides a method for disinfecting characterised in that a substrate to be disinfected is contacted with a disinfectant prepared from a storage stable, aqueous acidic solution as hereinbefore defined.

The aqueous acidic solutions according to the present invention comprise at least one ester peracid defined by having the general chemical formula:

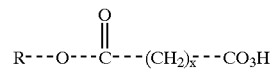

where R represents an alkyl group having from 1 to 4 carbons and x is from 1 to 4. When R has 3 or 4 carbons, the alkyl group can be linear or branched, i.e. the alkyl group can be n- or isopropyl, or n-, iso- or tertiary butyl. Preferably, R is a methyl group. In many cases, the value of x is 2, 3 or 4.

In a particular embodiment, the solution according to the present invention comprises a mixture of the ester peracids where x is 2, 3 and 4, i.e. a mixture of the monoesters of peradipic, perglutaric and persuccinic acids. In a particularly preferred embodiment, the major fraction of the ester peracids present in the composition has x equal to 3.

The solutions according to the present invention have a pH in the range of from 1 to 5, and preferably from 1.5 to 4. In certain embodiments, the pH of the solutions is greater than 1.75, and may be greater than 2, for example 2.5 or more. A pH in the range of from 3 to 3.5 may be advantageous in certain embodiments. The ester peracid solutions according to the present invention can often exist as equilibrium mixtures in aqueous solution, in which the ester peracid is in equilibrium with water, hydrogen peroxide and the non-peroxidised acid. The equilibrium obeys the following general equation:

where R represents hydrogen or an organic radical. It will be readily apparent that, for a fixed concentration of one component, the relative concentrations of the individual components can vary over a wide range and still be at equilibrium. When a solution of an ester peracid is not at equilibrium, chemical reaction takes place such that the composition of the mixture changes towards that of the equilibrium composition.

The solutions according to the present invention have the advantage of storage stability, ie the activity of the ester peracid component of the solution is retained through extended periods of storage. Depending on the application, the desired storage stability can range from periods of several days, for example 10 or more days, to periods of several, for example 4 or more, weeks, and even several, for example, 3 or more, months.

The ester peracids are often present in the solutions, either in use or in storage, at a total concentration of from about 0.0001 to about 15% by weight of the solution, preferably from about 0.05 to about 10% by weight, and more preferably from about 0.1 to about 5% by weight. It will be recognised that ester peracid solutions for storage and/or transportation, particularly where a dilution to produce an in use composition will be employed, will often comprise at least 0.1% by weight ester peracid, preferably at least 1% by weight ester peracid.

The total concentration of non-peroxidised ester acids is typically up to about 15% by weight of the solutions, although concentrations of up to 30% can be employed in certain embodiments, often from about 0.05 to about 10%, most often from about 1% to about 9%.

Hydrogen peroxide is typically present in the solutions at a concentration of up to 30% by weight, with concentrations in the range of from 15 to 25%, for example about 20% by weight, giving particularly good results in certain embodiments. In other embodiments, the concentration of hydrogen peroxide is often from about 0.5 to about 15%, more often from about 1 to about 10%.

Optional components in solutions according to the present invention comprise stabilisers, inert inorganic salts, surfactants, dyes, perfumes, corrosion inhibitors and, where thickening is not achieved by a combination of components present for other purposes, thickeners. The optional components can be present at a wide range of concentrations, but in many cases, the total concentration of these optional components will not exceed 25% by weight.

Stabilisers can desirably be employed to improve the storage stability of solutions according to the invention and are especially desirable where the proposed application involves the likely chance that the ester peracid will be contacted with compounds known to cause decomposition, for example transition metal ions. Suitable chelating agents are often aminopolycarboxylic acids or salts thereof such as EDTA or DTPA, and/or carboxylic acid substituted N-containing heterocyclics, such as 8-hydroxyquinoline or picolinic or dipicolinic acid, and organopolyphosphonates, including hydroxyethylidenediphosphonic acid, and alkyleneaminomethylene phosphonic acids such as ethylene diaminotetra methylene phosphonic acid, cyclohexane-1,2-diaminotetramethylene phosphonic acid and diethylenetriaminepenta methylene phosphonic acid. A combination of an organophosphonate and an N-heterocyclic carboxylic acid is particularly suitable. The amount of chelant in the solution is at the discretion of the formulator, but is preferably greater than 0.25% and often not greater than about 1.5%, calculated as active material therein.

The surfactants which can be employed herein can be nonionic, anionic, cationic, or amphoteric. Generally, the surfactants contain at least one hydrophobic group, e.g. an aliphatic hydrocarbon group containing at least 8 carbon atoms, and often from 10 to 26 carbon atoms, the aliphatic group often being acyclic, but sometimes containing an alicyclic group, or the hydrophobic group can be an alkaryl group containing at least 6 and preferably up to 18 aliphatic carbon atoms. The surfactant contains in addition at least one water-solubilising group for example a sulphonate, sulphate, or carboxylic group which is linked either directly or indirectly to the hydrophobic group. Linking members can include residues of polyhydric alcohols containing etheric or esteric linkages, for example derived from ethylene glycol, propylenie glycol, glycerine or polyether residues. The surfactants can be soap or be synthetic, for example as described in chapter 2 of synthetic Detergents by A. Davidsohn and B. M. Milwidsky, 6th Edition published in 1978 by George Godwin Limited, and methods of making them are described in chapter 5 of the same book. Amongst anionic surfactants described on pages 11–23 of the aforementioned book, sulphonates and sulphates are of special practical importance. The sulphonates include, for example, alkaryl sulphonates, and particularly alkyl benzene sulphonates, the alkyl group preferably being a straight chain containing 9 to 15 carbon atoms, of which one of the most commonly employed surfactants is linear dodecyl benzene sulphonate. Other anionic sulphonates which are useful in solutions herein include olefin sulphonates, obtained, for example, by sulphonating primary or secondary aliphatic mono-olefins, alkane sulphonates, especially linear alkane sulphonates, and hydroxy alkane sulphonates and disulphonates, especially 3-, 4-, and 5-hydroxy-n-alkyl sulphonates in which the alkyl group contains any even number from 10 to 24 carbon atoms. Other desirable anionic surfactants include alcohol sulphates, preferably linear, having a chain length of at least 10 carbon atoms and sulphated fatty acid alkanolamides. Other sulphates comprise sulphated nonionic surfactants as for example alkylphenoxyethylene oxide ether sulphate in which the alkyl groups contain from about 8 to 12 carbon atoms and there are 1 to 10 units of ethylene oxide in each molecule. Yet other sulphate surfactants comprise alkyl ether sulphates where the alkyl group contains from 10 to 20 carbon atoms, preferably linearly and each molecule contains from 1 to 10 preferably from 1 to 4 molecules or ethylene oxide. Further anionic surfactants include phosphate derivatives of the ethylene oxide based nonionic surfactants described herein.

It is of considerable advantage that at least a proportion of the anionic surfactant be in liquid form or readily liquifiable.

In many suitable classes of anionic surfactants the counter ion is a monovalent metal ion, often a sodium or potassium ion, or a quaternary ammonium cation derived for example from ethanolamine or isopropylamine.

In practice, cationic detergents are normally not present in the same composition as anionic surfactants, but when cationic detergents are used they are frequently quaternary ammonium salts such as tetraalkyl ammonium salts in which at least one of the alkyl group contains at least 10 carbon atoms or quaternary pyridinium salts substituted by an alkyl chain of at least 10 carbon atoms. Although quaternary ammonium halides, commonly chlorides, can be employed, particularly where the quaternary ammonium halide and ester peracid are combined shortly before use, in many embodiments it is preferred to employ non-halide quaternary ammonium salts. The use of non-halide quaternary ammonium salts is particularly preferred where the solution containing the ester peracid and quaternary ammonium salt are to be stored for any significant period. The use of quaternary ammonium halides in such solutions for storage can cause decomposition of the ester peracid by oxidation of the halide. Examples of non-halide quaternary ammonium salts include sulphates, methosulphates, ethosulphates, hydroxides, acetates, saccharinates, phosphates and propionates.

A considerable proportion of nonionic surfactants suitable for use in the present invention comprises condensation products of ethylene oxide and possibly propylene oxide. One class of such nonionic surfactants which is of special importance comprises water soluble condensation products of alcohols containing from 8 to 18 carbon atoms with an ethylene oxide polymer often containing at least 5 moles of ethylene oxide per molecule of surfactants, e.g. from 7 to 20 moles of ethylene oxide. Other nonionic surfactants comprise water soluble condensates of alkyl phenols or alkyl naphthols with an ethylene oxide polymer normally containing from 5 to 25 moles of ethylene oxide per mole of alkyl phenol or alkyl naphthol. The alkyl group normally contains from 6 to 12 carbon atoms and is frequently linear. As an alternative to the hydrophobic moiety of the nonionic surfactant being linked to the hydrophilic moiety by an ether link as in alcohol or phenol/ethylene oxide condensates, the linkage can be an ester group. The hydrophobic moiety is normally the residue of a straight chain aliphatic acid containing from 8 to 22 carbon atoms and more particularly lauric, stearic and oleic residues. In one class of nonionic ester surfactants, the hydrophilic moiety often comprises polyethylene oxide, frequently in the ratio of from 5 to 30 moles of ethylene oxide per mole of the fatty acid residue. It will be recognised that both mono and di esters can be employed. Alternatively it is possible to employ as the hydrophilic moiety glycerol, thereby producing either mono or di glycerides. In a further group, the hydrophilic moiety comprises sorbitol. A further class of nonionic surfactants comprise alkanolamides which can be obtained when a C10 to C22 amide is condensed with a polyethylene oxide or polypropylene glycol hydrophilic moiety or moieties. Semipolar detergents include water soluble amine oxides, water soluble phosphine oxides and water soluble sulphur oxides, each containing one alkyl moiety of from 10 to 22 carbon atoms and two short chain moieties selected from the groups of alkyl and hydroxyalkyl groups containing 1 to 3 carbon atoms.

Useful amphoteric surfactants include derivatives of aliphatic quaternary amrhonium, sulphonium and phosphonium compounds in which the aliphatic moieties can be linear or branched, or two of which can join to form a cyclic compound, provided that at least one of the constituents comprises or contains a hydrophobic group containing from about 8 to 22 carbon atoms and the compound also contains an anionic water solubilising group, often selected from carboxylic, sulphate and sulphonates.

Non-surfactant thickeners which may be employed comprise cross linked poly(acrylates), natural gums such as xanthan or rhamsan gum, cellulose derivatives such as carboxymethyl cellulose and silicates.

The process for preparing storage stable, aqueous acidic solutions according to the present invention comprising at least one ester peracid, comprises contacting an aqueous solution of one or more carboxylic compounds having the general formula:

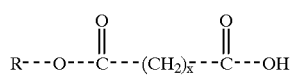

where x is from 1 to 4, R represents an alkyl group having from 1 to 4 carbons, and x is from 1 to 4, with an inorganic peroxygen compound at a pH of less than 4 until at least some ester peracid is formed. The contact is normally effected at a temperature of from about 0° C. to about 50° C., and in many embodiments is effected at a pH of 3 or less, particularly preferably 2.5 or less. Where the pH of the resultant ester peracid solution produced is less than 1, its pH is adjusted to be in the range of from 1 to 5.

The inorganic peroxide, which is preferably hydrogen peroxide but may be a persalt such as sodium perborate mono and tetrahydrates, can be present in an equimolar ratio to the ester acid or acid derivative, but in many cases it is desirable to employ a molar excess of the inorganic peroxide. It will be appreciated that as the solution of ester peracid produced will tend to form an equilibrium composition, the choice of concentrations of the starting materials will to a large extent determine the final composition produced, unless subsequent processing, e.g. dilution, cause this to be changed.

In certain embodiments where particularly rapid formation of the ester peracid is desired, the process for preparing storage stable, aqueous acidic solutions according to the present invention can be carried out in the presence of a catalytic amount of a strong acid, for example sulphuric acid, phosphoric acid and organic sulphonic acids such as methane sulphonic acid, to increase the rate of formation of the ester peracid by lowering the solution pH. A pH in the range of from 0 to 1 is often employed. When employed, the strong acids will often be present in an amount ranging from 0.1 to 5% by weight of the solution. However, it will be recognised that the presence of a strong acid species causes relatively rapid hydrolysis of the ester function. Loss of the ester function not only directly causes loss of ester peracid, but also indirectly, by removing ester acid from the equilibrium, which causes ester peracid to revert to ester acid and hydrogen peroxide. Therefore, where a strong acid is employed, to produce a storage stable solution of an ester peracid, the strong acid should be neutralized by the addition of a corresponding amount of alkali. Alkalis that can be employed for this neutralization include in particular alkali metal hydroxides and ammonia, particularly sodium hydroxide. In preferred embodiments of the present invention, a strong acid catalyst is employed, and the solution allowed to react in the presence of the strong acid until the ester peracid concentration reaches the desired concentration. At this point, alkali is then added to raise the pH of the solution to a value where the catalytic production of ester peracid is reduced or prevented, and the hydrolysis of the ester is also reduced or prevented, often a pH in the range of from 1.5 to 5, and particularly from 2.5 to 4, for example a pH of from 3 to 3.5.

In another preferred embodiment, the ester peracids according to the invention are prepared by controlled addition of an aqueous solution of hydrogen peroxide, having a concentration of up to 90% w/w and often greater than about 30% w/w, preferably from about 65% to about 88% w/w hydrogen peroxide to an aqueous solution of the ester acid starting material plus any other optional components with gentle agitation. Preferably, ambient temperature is employed, with typical values ranging from about 10° C. to about 30° C. The time required to allow the ester peracid solution to reach equilibrium will depend on many factors, including the temperature and the presence and amount of any acid catalysts employed. Typical times are often between 1 day and about 30 days.

In a particularly preferred embodiment, the source of ester acid starting material comprises a mixture of the monomethyl esters of succinic, adipic and glutaric acid.

In some embodiments of the present invention, the ester acid is obtained in situ by hydrolysis of a diester, optionally in the presence of the inorganic peroxygen compound. Conditions similar to those employed for the strong acid catalysed production ester peracid are employed, followed by subsequent addition of alkali to mitigate against the detrimental effects of the strong acid on the ester function. The advantage of such an approach is that it enables the more readily available diesters to be employed as starting materials.

The method for disinfection according to the present invention comprises contacting the substrate to be disinfected with a storage stable, aqueous acidic solution of an ester peracid, or with a solution prepared from one. The solution may be employed without dilution, or may be diluted. When the compositions are diluted, the dilution is usually chosen to give a concentration of ester peracid in solution of between about 1 part per million and 10,000 parts per million, depending on the substrate.

The disinfecting method may utilise a very wide range of temperatures, typically ranging from about 4° C. to the boiling point of the solution employed as a disinfectant. In many cases, especially if the disinfectant is being applied manually using, e.g. a cloth, the temperature will be limited by the maximum temperature which can be tolerated comfortably by the operative, and is unlikely to be greater than 60° C.

The disinfection process can be employed to treat a wide range of substrates. Many of the treatable substrates are either liquid or solid. A contaminated gaseous substrate can be treated conveniently by spraying with a dilute solution of the invention biocidal combination or by bubbling the gas through a bath of the invention peracid solution. One type of liquid substrate comprises micro-organism contaminated aqueous media such as recirculating process waters, or aqueous effluents prior to discharge. Such process waters and effluents occur in many different industries and can be contaminated by bacteria, algae, yeasts and more rarely by viruses. Without limiting to the following industries, contaminated process waters are prevalent during the processing of plant and animal materials, including the paper and pulp industries, food processing e.g. the sugar refining industry, brewing, wine-making and alcohol distilling industries, effluents from straw treatments, discharges from sewage treatment works, including partially treated or merely filtered discharges of sewage through pipelines extending out to sea, meat processing factories, carcass rendering activities and from the rearing of livestock. Other liquid substrates include irrigation water in the horticulture industry. A further important source of contaminated aqueous media comprises cooling waters either industrially or arising from air conditioning units installed in large buildings; such as hotels, offices and hospitals. The invention compositions can be employed to treat non-aqueous liquid media, such as cutting oils.

Notwithstanding the foregoing, the invention compositions are seen as of particular value for disinfection in those areas which come into contact with humankind. Thus they can be employed to disinfect solids, including hard surfaces, or contaminated articles intended for re-use in the food processing, animal rearing, horticulture, catering, domestic or hospital environments. Hard surfaces can be made from metals, wood, ceramics, glass, and plastics and can include work-benches, walls, floors, sanitary ware, plant or apparatus, containers, tools, machinery, plant and pipework. It will be recognised that for such hard surfaces, it is often convenient to immerse smaller articles in a solution of the invention biocidal composition, and for larger applications, a spray or the like distribution means can be easier to employ. The process can also be contemplated for disinfecting water absorbent materials such as infected linen or especially soiled babies' nappies that are often made from terry towelling. The invention compositions can be used to disinfect harvested plants or plant products including seeds, corms, tubers, fruit, and vegetables. Alternatively, the invention compositions can be used to treat growing plants, and especially crop growing plants, including cereals, leaf vegetables and salad crops, root vegetables, legumes, berried fruits, citrus fruits and hard fruits.

It will none the less also be recognised that the peracid solutions produced by the invention process may also be employed, if desired, for the other purposes for which peracids are used, including bleaching or as a bleach additive in washing processes.

Having described the invention in general terms, specific embodiments thereof will now be illustrated by way of example only.

Example 1

Preparation of monomethyl perglutarate (MMPG)

Aqueous solutions comprising 10% w/w monomethylglutarate (MMG) and 10% w/w $H_2O_2$ (Sample A), 10% w/w MMG and 20% w/w $H_2O_2$ (Sample B), 20% w/w MMG and 10% w/w $H_2O_2$ (Sample C), 20% w/w MMG and 20% w/w $H_2O_2$ (Sample D), 30% w/w MMG and 10% w/w $H_2O_2$ (Sample F), and 30% w/w MMG and 20% w/w $H_2O_2$ (Sample E) were prepared by dissolving monomethylglutarate in water. To this solution was added with gentle stirring, the required amount of hydrogen peroxide (85% w/w) over a period of 10 minutes. The solutions each had a pH in the range of 1.5 to 2. The solutions were then stored at ambient temperature for 12 days and analysed by HPLC at intervals during this storage. The HPLC analysis employed an Apex octadecyl column (25 cm, 5 microns) available from Jones Chromatography. The eluent was 75:25 water plus 0.25% acetic acid:methanol at an elution rate of 1 ml per minute. Ultra-violet detection at 210 nm was employed. The analysis showed a peak after 6.8 minutes which was attributed to monomethylperglutarate. To confirm this as a peracid peak, addition of thiodiglycol to the sample caused this peak to disappear. In addition to the MMPG, the concentrations of monomethylglutarate (MMG), glutaric acid (GA) and perglutaric acid (PGA) were also monitored. The results are given in Table 1 below.

TABLE 1

Analysis of MMPG Samples (All % w/w)

| Sample | Time (days) | % MMG | % GA | % PGA | % MMPG |
|---|---|---|---|---|---|
| A | 5 | 8.8 | 0.9 | 0.13 | 0.17 |
|   | 12 | 7.85 | 1.46 | 0.29 | 0.4 |
|   | 21 | 7.6 | 2.0 | 0.15 | 0.24 |
| B | 5 | 8.1 | 0.8 | 0.31 | 0.73 |
|   | 12 | 7.09 | 1.07 | 0.65 | 1.2 |
|   | 21 | 6.86 | 1.59 | 0.63 | 0.93 |
| C | 5 | 17.3 | 1.98 | 0.2 | 0.47 |
|   | 12 | 15.84 | 3.06 | 0.44 | 0.66 |
|   | 21 | 15.1 | 4.37 | 0.22 | 0.39 |
| D | 1 | 18.5 | 1.1 | trace | 0.36 |
|   | 5 | 15.8 | 1.58 | 0.78 | 1.8 |
|   | 12 | 13.48 | 1.98 | 1.52 | 3.02 |
|   | 21 | 12.56 | 2.77 | 1.73 | 2.92 |
| E | 1 | 27.4 | 1.65 | trace | trace |
|   | 5 | 26.1 | 2.58 | 0.36 | 1.0 |
|   | 12 | 24.2 | 3.99 | 0.6 | 1.23 |
|   | 21 | 22.8 | 6.3 | 0.32 | 0.64 |
| F | 1 | 27.6 | 1.56 | 0.2 | 0.59 |
|   | 5 | 23.6 | 1.13 | 1.1 | 3.1 |
|   | 12 | 20.3 | 2.85 | 2.1 | 4.77 |
|   | 21 | 19.59 | 4.22 | 2.12 | 4.05 |

Analysis of the solutions by titration with ceric sulphate solution showed that after 21 days, Sample A comprised 9.7% w/w $H_2O_2$, Sample B comprised 19.5% w/w $H_2O_2$, Sample C comprised 8.8% w/w $H_2O_2$, Sample D comprised 19% w/w $H_2O_2$, Sample E comprised 8.5% w/w $H_2O_2$, and Sample F comprised of 17.2% w/w $H_2O_2$. The results clearly show the storage stability of the solutions according to the present invention. The storage stability results for samples B, D and F, ie those samples comprising about 20% w/w hydrogen peroxide, are particularly advantageous.

Comparison 2

Preparation of monomethyl Derglutarate (MMPG) in the presence of strong acid, without subsequent pH adjustment 5.39 g of monomethyl glutarate, 0.59 g sulphuric acid (98% w/w) and 0.189 g hydroxyethylidenediphosphonic acid, commercially available in the UK under the Trade name DEQUEST 2010, were dissolved in 37.59 g of demineralised water. To this solution was added with gentle stirring, 5.99 g of hydrogen peroxide (85% w/w) over a period of 10 minutes, producing a solution with a pH of about 0.5. The solution was then stored for 2 weeks at room temperature (ca 20° C.). Analysis of the solution by the HPLC method given in Example 1 above showed that after 1 day, a mixture comprising MMPG and PGA an approximately 1:1 w/w ratio had been produced. However, after 2 weeks, substantially no MMPG remained. It was also observed that the concentration of MMG in the solution had significantly decreased, with a corresponding increase in glutaric acid concentration. These results indicated that the solution was not storage stable, probably on account of hydrolysis of the ester function in both MMPG and MMG.

Example 3

Preparation of MMPG plus Stabiliser 5.39 g of monomethyl glutarate and 0.189 g hydroxyethylidenediphosphonic acid, commercially available in the UK under the Trade name DEQUEST 2010, as stabiliser, were dissolved in 37.59 g of demineralised water. To this solution was added with gentle stirring, 5.99 g of hydrogen peroxide (85% w/w) over a period of 10 minutes. The solution was then stored for about 2 weeks. The solution was found to have no discernible odour.

Example 4

Preparation of monomethyl Dersuccinate (MMPS)

Monomethyl succinate (5 g) was dissolved in demineralised water (38.7 g). To this solution was added 86% hydrogen peroxide solution (6 g) over a 10 minute period with gentle stirring at room temperature and then hydroxyethylidenediphosphonic acid, commercially available in the UK under the Trade name DEQUEST 2010 (0.18 g). The solution was allowed to stand for about 2 weeks, and was found to have no discernible odour.

Example 5

Preparation of monomethyl ester peracid from mixture of monomethyl esters of adipic, glutaric and succinic acids Monomethyl glutarate (3.3 g), monomethyl adipate (0.6 g) and 1.2 g monomethyl succinate were dissolved in demineralised water (38.7 g). To this solution was added 86% hydrogen peroxide solution (6 g) over a 10 minute period with gentle stirring at room temperature and then hydroxyethylidenediphosphonic acid, commercially available in the UK under the Trade name DEQUEST 2010 (0.18 g). The solution was allowed to stand for about 2 weeks and was found to have no discernible odour.

Example 6

Disinfection Trials

The solutions prepared in Examples 3, 4 and 5 were screened for activity against bacteria (*Pseudomonas aeruginosa* and *Staphylococcus aureus*) and a yeast (*Saccharomyces cerevisiae*) employing the method described by M. G. C. Baldry in the Journal of Applied Bacteriology, 1983, vol 54, pp417 to 423, with a contact time of 5 minutes at 20° C. The pH of the solutions was varied as detailed in Table 2 below. The solutions were employed at 20 ppm peracid avox against the bacteria and at 50 ppm peracid avox against the yeast. Comparative tests were also carried out employing the same concentrations of peracetic acid by weight prepared by dilution of a peracid solution containing 1% w/w peracetic acid, 6% w/w hydrogen peroxide and 9% w/w acetic acid. The results of the trial are given in Table 2 below. Table 2 also includes comparative results under the same conditions against the yeast *Saccharomyces cerevisiae* for monoperglutaric acid solution (PGA), monopersuccinic acid solution (PSA) and a solution comprising a 45:27:27 weight ratio of monoperadipic acid-:monoperglutaric acid:monopersuccinic acid (AGS).

TABLE 2

Results of Disinfection Trial

Logarithmic Reduction Factor

| | Ps. aeruginosa | | Staph. aureus | | Saccha. cerevisiae | | |
|---|---|---|---|---|---|---|---|
| Example pH | 5 | 6 | 9 | 5 | 6 | 5 | 6 | 9 |
| 3 | 5.0 | 5.0 | 5.3 | 5.4 | 5.4 | 5.0 | 4.3 | 3.1 |
| 4 | 5.3 | 5.0 | 5.1 | 5.4 | 5.5 | 5.1 | 5.2 | 3.6 |
| 5 | 5.0 | 5.1 | 5.0 | 5.5 | 5.2 | (not measured) | | |
| PAA | 5.0 | 4.9 | 5.0 | 5.4 | 5.0 | 5.5 | 5.3 | 3.0 |
| PGA | | | | | | <3.0 nm | | <3.0 |
| PSA | | | | | | <3.0 nm | | <3.0 |
| AGS | | | | | | <3.0 nm | | <3.0 | nm = not measured

The results showed that against the bacteria and the yeasts, the ester peracid solutions according to the present invention gave a disinfection performance that was broadly comparable to that of peracetic acid. The good performance achieved against the yeasts is particularly surprising, given the poor activity of the PGA, PSA and AGS solutions. During the disinfection trial, it was observed that the odour of the peracetic acid solution was unpleasant, but that the odour from any of the solutions according to the present invention was not discernible, thus demonstrating that, on an equivalent performance basis, the compositions according to the present invention demonstrate lower odour.

Example 7

Preparation of monobutyl perglutarate

Monobutyl perglutarate was prepared by the method of Example 3 except that monobutyl glutarate (prepared by reaction between butan-1-ol and glutaric acid at a 1:1 mole ratio) was employed. After standing for 1 day, the solution was analysed and found to comprise 0.08% monobutyl perglutarate and 10.2% hydrogen peroxide. After 2 weeks storage at room temperature, the solution composition was found to be the same, within the limits of experimental error. The composition had no discernible odour.

Example 8

Preparation of monobutyl persuccinate

Monobutyl persuccinate was prepared by the method of Example 3 except that monobutyl succinate (5 g) (prepared by reaction between butan-1-ol and succinic anhydride at a 1:1 mole ratio) was employed. After standing for 1 day, the solution was analysed and found to comprise 0.05% monobutyl persuccinate and 10.9% hydrogen peroxide. After 2 weeks storage at room temperature, the solution composition was found to comprise 0.12% monobutyl persuccinate and 10.4% hydrogen peroxide. The composition had no discernible odour.

Comparison 9

Preparation of monooctyl persuccinate

Monooctyl persuccinate was prepared by the method of Example 5 except that monooctyl succinate (prepared by reaction between octan-1-ol and succinic anhydride at a 1:1 mole ratio) was employed.

Examination of the solution produced showed that it had formed a 2 phase system.

Example 10

Disinfection Trials

The solutions prepared in Examples 7 and 8 were screened for disinfection activity by the same general method as in Example 6 above. The pH of the solutions was varied as detailed in Table 3 below. The results of the trial are given in Table 3 below.

TABLE 3

Results of Disinfection Trial

| | Logarithmic Reduction Factor | | | | | | | |
|---|---|---|---|---|---|---|---|---|
| | Staph. aureus | | | Ps. aeruginosa | | Saccha. cerevisiae | | |
| Solution pH | 5 | 6 | 9 | 5 | 6 | 5 | 6 | 9 |
| 7 | 4.0 | 3.8 | 3.9 | 4.2 | 4.1 | >5 | <2.5 | 3.4 |
| 8 | 4.0 | 3.9 | 3.9 | 4.4 | 3.9 | >5 | >5 | >5 |
| PAA | 4.1 | 3.9 | 3.8 | 4.3 | 4.3 | >5 | >5 | <2.5 |

The results showed that against the bacteria, the ester peracid solutions according to the present invention gave a disinfection performance that was broadly comparable to that of peracetic acid. Against the yeasts, the disinfection performance was again at least comparable with peracetic acid, and in the case of the solution of Example 8 at pH 9, was marlkedly superior to peracetic acid. This represents surprisingly good performance as >C4 aliphatic peracids are known to have very poor activity against yeasts. During the disinfection trial, it was again observed that the odour of the peracetic acid solution was unpleasant, but that the odour from any of the solutions according to the present invention was not discernible, thus demonstrating that, on an equivalent performance basis, the solutions according to the present invention demonstrate lower odour.

Comparison 11

A solution of the same composition as Example 1, sample A was prepared, except that the solution was buffered to pH 4 on addition of the hydrogen peroxide. The solution was observed to contain substantially no ester peracid after 14 days storage at room temperature.

Comparison 12

A solution of the same composition as Example 1, sample A was prepared, except that the pH of the solution was adjusted to 0.5 on addition of the hydrogen peroxide. The solution was observed to contain substantially no ester peracid after 14 days storage at room temperature.

The results of Comparisons 11 and 12 demonstrate the importance of control of the pH during the preparation of the compositions according to the present invention.

Example 13 and Comparison 14

A parent solution of the same composition as Example 1, sample A was prepared, except that the solution also comprised 1% sulphuric acid. The pH of the solution was about 0.5. After 1 day's storage at room temperature, the solution was analysed by the HPLC method of Example 1. The solution was divided into 2 portions. In Example 13, the pH of the solution was increased to be about 2 by the addition of 47% w/w sodium hydroxide solution. In Comparison 14, the pH of the solution was not adjusted. The 2 portions were stored at room temperature for a further 8 days (ie 9 days storage in total). The portions were then analysed by the HPLC method of Example 1. The results are given in Table 4 below.

TABLE 4

| Sample | Time (days) | % MMG | % GA | % PGA | % MMPG |
|---|---|---|---|---|---|
| Parent | 1 | 5.69 | 2.97 | 0.94 | 0.4 |
| Example 13 | 9 | 5.67 | 3.65 | 0.29 | 0.39 |
| Comp 14 | 9 | 1.9 | 5.5 | 2.36 | 0.21 |

The results show clearly that after 9 days storage, the solution of Example 13 retains substantially the same MMPG concentration as the Parent solution, whereas that of Comparison 14 had reduced to almost half. This demonstrates the advantage of increasing the pH of solutions prepared by the use of a strong acid catalyst. It also demonstrates the superior stability of the aqueous acidic solutions according to the present invention.

What is claimed is:

1. A storage stable, aqueous acidic equilibrium solution containing a peracid component in solution and having a pH in the range of from 1 to 5, said peracid component comprising at least one ester peracid having the general formula:

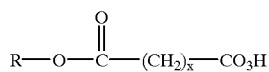

where R represents an alkyl group having from 1 to 4 carbons and x is from 1 to 4, said ester peracid being present in an amount of from 0.1% to 15% by weight of the solution.

2. A solution according to claim 1, wherein the pH of the solution is from 1.5 to 4.

3. A process for preparing a storage stable, aqueous acidic equilibrium solution comprising at least one ester peracid, which comprises contacting an aqueous solution comprising at least one carboxylic compound having the general formula:

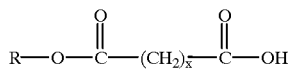

where x is from 1 to 4 and R represents an alkyl group having from 1 to 4 carbons, with an inorganic peroxygen compound in the presence of an acid catalyst to produce in said solution, at a pH of less than 1, an ester peracid having the general formula:

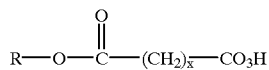

where R represents an alkyl group having from 1 to 4 cabons and x is from 1 to 4, and, after the ester peracid has reached a desired concentration, adjusting the pH of the solution to be in the range of from 1 to 5.

4. A process according to claim 3, wherein the inorganic peroxygen compound comprises hydrogen peroxide.

5. A process according to claim 4, wherein the hydrogen peroxide comprises an aqueous solution having a concentration of hydrogen peroxide of from about 65% to about 88% by weight.

6. A solution according to claim 1 or 2 wherein x is 2, 3 or 4.

7. A solution according to claim 1 or 2 wherein R is a methyl group.

8. A solution according to claim 1 or 2, wherein the ester peracid is present in the solution in an amount 0.1% to about 5% by weight of the solution.

9. A solution according to claim 1 or 2, wherein the ester peracid comprises monomethylperglutaric acid.

10. A solution according to claim 1 or 2, wherein the ester peracid comprises monomethylperadipic acid.

11. A solution according to claim 1 or 2, wherein the ester peracid comprises monomethylpersuccinic acid.

12. A solution according to claim 1, wherein the solution comprises from 15% to 25% by weight hydrogen peroxide.

13. A solution according to claim 1, wherein said solution includes up to 30% by weight of hydrogen peroxide.

14. A solution according to claim 13, wherein said solution includes up to 30% by weight of a non-peroxidized ester acid corresponding to said ester peracid.

15. A solution according to claim 13 wherein said solution includes at least one optional component selected from the group consisting of stabilizers, inert organic salts, surfactants, dyes, perfumes, corrosion inhibitors, and thickeners, and wherein the total amount of said at least one optional component is not more than 25% by weight of the solution.

16. A solution according to claim 1 wherein said at least one ester peracid comprises a mixture of monoesters of peradipic, perglutaric, and persuccinic acids.

17. A solution according to claim 1 wherein said at least one ester acid is generated in situ by hydrolysis of a diester.

18. A solution according to claim 1 wherein said ester peracid is present in an amount of at least 1% by weight of the solution.

19. A process for the storage of a aqueous acidic equilibrium solution containing a peracid component, said peracid component comprising at least one ester peracid having the general formula:

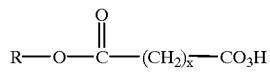

where R represents an alkyl group having from 1 to 4 carbons and x is from 1 to 4, said ester peracid being present in an amount of from 0.1% to 15% by weight of the solution, said process comprising storing said solution at a pH of from 1 to 5.

20. A process according to claim 19 wherein said storing is performed for a period of at least 10 days.

21. A method for disinfecting which comprises:

providing a storage stable, aqueous acidic equilibrium solution containing a peracid component in solution and having a pH in the range of from 1 to 5, said peracid component comprising at least one ester peracid having the general formula:

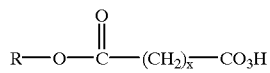

where R represents an alkyl group having from 1 to 4 carbons and x is from 1 to 4, said ester peracid being present in an amount of from 0.1% to 15% by weight of the solution;

diluting said storage stable solution to produce a dilute aqueous solution containing said ester peracid in said dilute aqueous solution in an amount of from 1 to 10,000 ppm; and contacting a substrate to be disinfected with said dilute aqueous solution.

22. A method according to claim 3 wherein said ester peracid is present in said solution in an amount of up to 15% by weight of the solution.

23. A method according to claim 3 wherein said catalyst comprises a strong acid in an amount of from 0.1 to 5% by weight of the solution.

24. A method according to claim 3 wherein said adjusting the pH of the solution comprises adding alkali to the solution to adjust said pH to be in the range of 1.5 to 5.

25. A method according to claim 24 wherein said pH is adjusted to be in the range of 2.5 to 4.

26. A method according to claim 24 wherein said pH is adjusted to be in the range of 3 to 3.5.

* * * * *